US00PP28997P2

(12) United States Plant Patent
Bradford et al.

(10) Patent No.: US PP28,997 P2
(45) Date of Patent: Feb. 27, 2018

(54) PLUM TREE NAMED 'PLUMSWEET XX'

(50) Latin Name: *Prunus salicina*
Varietal Denomination: Plumsweet XX

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 15/530,229

(22) Filed: Dec. 15, 2016

(51) Int. Cl.
*A01H 5/08* (2006.01)

(52) U.S. Cl.
USPC ..... Plt./198

(58) Field of Classification Search
USPC ..... Plt./198
See application file for complete search history.

(56) References Cited

U.S. PATENT DOCUMENTS

PP15,809 P2 6/2005 Bradford
PP18,687 P2 4/2008 Bradford

*Primary Examiner* — Annette H Para

(57) ABSTRACT

The present invention relates to a plum tree, *Prunus salicina*, and more particularly to a new and distinct variety broadly characterized by a medium to large size, vigorous, hardy, and productive tree. Being self-unfruitful, the present variety requires cross pollination from an apricot, interspecific, or plum that blooms during the early season, such as 'Yummygem' plum tree (U.S. Plant Pat. No. 15,809). The present variety produces a moderate amount of blossoms that produce a medium amount of pollen to entice good bee activity to facilitate pollination. The fruit matures under the ecological conditions described during early June, with first picking on May 29, 2016. The fruit is uniformly medium to large in size, a red and green two-tone in skin color, full red in flesh color, clingstone in type, somewhat oblate in shape, firm in texture, juicy, sweet, and very good in flavor.

1 Drawing Sheet

Botanical classification: *Prunus salicina.*
Varietal denomination: 'PLUMSWEET XX'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree which has been denominated varietally as 'Plumsweet XX'.

During 2007 we gathered fruit from several different early maturing red flesh plum trees that were located on our ranch in Le Grand, Calif. The seeds were removed, cracked, stratified and germinated as a group with the label "EY RF (OP)". They were grown as seedlings on their own root in our greenhouse and upon reaching dormancy transplanted to a cultivated area of our experimental orchard located near Le Grand, Calif. in Merced County (San Joaquin Valley). During the spring of 2011 the claimed variety was selected by us as a single plant from the group of seedlings described above. Subsequent to origination of the present variety of plum tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is most similar to 'Plumsweet VI' interspecific tree (U.S. Plant Pat. No. 18,687), by being self-unfruitful and by producing fruit that ripens in the early season and that is a red and green two-tone with freckles in skin color, clingstone in type, firm in texture, juicy, and sweet in flavor, but is distinguished therefrom by being easier to set and by producing fruit that is larger in size and darker red in flesh color.

SUMMARY OF VARIETY

The present plum variety is characterized by a medium to large size, vigorous, hardy, and productive tree. Being self-unfruitful, the present variety requires cross pollination from an apricot, interspecific, or plum that blooms during the early season, such as 'Yummygem' plum tree (U.S. Plant Pat. No. 15,809). The present variety produces a moderate amount of blooms that produce a medium amount of pollen to entice good bee activity to facilitate pollination. The fruit matures under the ecological conditions described during early June, with first picking on May 29, 2016. The fruit is uniformly medium to large in size, a red and green two-tone in skin color, full red in flesh color, clingstone in type, somewhat oblate in shape, firm in texture, juicy, sweet, and very good in flavor.

DRAWING

The accompanying photograph consists of four whole fruits positioned to display the characteristics of the skin color and form, one divided fruit to reveal the flesh and stone, a tip shoot growth, typical leaves, and three insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif. The fruit description was developed at the state of firm ripe on Jun. 9, 2016, on the original tree during its ninth growing season. The flower and bud descriptions were developed during the previous blooming season. All major color code designations are by reference to the Inter-Society Color Council, National Bureau of Standards. Common color names are also used occasionally.

It is to be noted that the 2016 fruit season in California was very warm during the spring and the ripening times of almost all varieties were about two weeks earlier than most years.

PARENTAGE

Seed parent: Unknown plum.
Pollen parent: Unknown plum.

TREE

Size: Medium to large, reaching and maintaining a height of 12' [3.66 m.] and a spread of 9' [2.74 m.] after nine growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-unfruitful, requiring cross pollination by a suitable early seasonal blooming apricot, interspecific, or plum, such as 'Yummygem' plum tree (U.S. Plant Pat. No. 15,809).

Bearing: Regular bearer, weather dependent, no crop failures observed as of yet.

Trunk:

- *Size.*—Medium, reaching a maximum diameter of 4½" [114.3 mm.] after the ninth growing season.
- *Texture.*—Medium, shaggy.
- *Bark color.*—A Grayish brown [61. gy.Br] and Dark grayish brown [62. d.gy.Br] variegation with Strong brown [55. s.Br] crevices present.
- *Lenticels.*—Approximate Number Per Square Inch: 12. Color: Moderate yellowish brown [77. m.yBr]. Average Size: ¼" [6.4 mm.] in length. The width is typically one fourth as much as the length. Shape: Eye-shaped.

Branches:

- *Size.*—Medium, scaffold diameter is 2½" [63.5 mm.] measured 12" above the crotch, limb diameter is 2" [50.8 mm.] measured 12" above the first fork.
- *Texture.*—Fairly smooth on first and second year wood, increasing roughness with age.
- *Color.*—1st Year Wood Topside: Grayish red [19. gy.R]. 1st Year Wood Underside: Strong yellow green [117. s.YG]. Older Wood: A Brownish gray [64. brGy] and Dark gray [266. d.Gy] variegation with Strong brown [55. s.Br] crevices present.
- *Lenticels.*—Number Per Square Inch: About 50 on second year wood. Color: Grayish yellowish brown [80. gy.yBr]. Average Size: Small, 1/32" [0.8 mm.] in length. The width is typically one fourth as much as the length. Shape: Rectangular.

Leaves:

- *Size.*—Medium to large. Average Length: 4" [101.6 mm.]. Average Width: 1¾" [44.5 mm.].
- *Arrangement.*—Alternate.
- *Thickness.*—Medium.
- *Form.*—Elliptical.
- *Apex.*—Acuminate.
- *Base.*—Acute with an average base angle of 75 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ⅜" [9.5 mm.]. Average Thickness: 1/16" [1.6 mm.]. Color: Topside is Moderate yellow green [120. m.YG] and the underside is Brilliant yellow green [116. brill.YG].
- *Stipules.*—Number: Mostly 2 per leaf, up to 6 per growing tip. Average Length: ⅜" [9.5 mm.]. Color: Moderate yellow green [120. m.YG] becoming Light olive brown [94. l.OlBr] with age.
- *Glands.*—Number: Mostly 2 per leaf. Position: Alternate, positioned at the intersection of the petiole and base of leaf blade. Form: Globose. Size: Small, 1/64" [0.4 mm.] in diameter. Color: Strong yellow green [117. s.YG] becoming Moderate reddish brown [43. m.rBr] in the center with age. Leaf buds: Pointed, medium.

Flower buds:

- *Hardiness.*—Hardy, with respect to central California blooming season.
- *Diameter.*—Typically 3/16" [4.8 mm.] 1 week before bloom.
- *Length.*—Typically ⅜" [9.5 mm.] 1 week before bloom.
- *Form.*—Free, not touching.
- *Surface.*—Non-pubescent.
- *Tip color.*—White [263. White].

Flowers: Perfect, complete, perigynous, usually a single pistil, about thirty stamens, five sepals and petal locations alternately positioned.

- *Average flower diameter.*—1⅛" [28.6 mm.].
- *Average flower depth.*—⅜" [9.5 mm.] when fully open.
- *Number of petals.*—Five, no double blossoms observed.
- *Petal shape.*—Oval.
- *Petal margin.*—Entire, smooth to slightly wavy.
- *Petal arrangement.*—Overlapping.
- *Average petal diameter.*—9/16" [14.3 mm.].
- *Average petal length.*—⅝" [15.9 mm.].
- *Petal apex.*—Rounded.
- *Petal base.*—Obtuse.
- *Petal color.*—White [263. White] on both sides.

*Anther color.*—Moderate orange yellow [71. m.OY].
*Pollen production.*—Moderate, enticing to bees.
*Stigma color.*—Vivid greenish yellow [97. v.gY].
*Stigma position.*—Located slightly above the average anther position.
*Stamen position.*—Typically located about 1/32" [0.8 mm] below the petals.
*Sepal color.*—Vivid yellow green [115. v.YG] on both sides.
*Sepal length.*—7/32" [5.6 mm.].
*Sepal width.*—5/32" [4.0 mm.].
*Sepal apex.*—Rounded to elliptical to match the width and length.
*Sepal margin.*—Fairly smooth with slight serrations toward the apex.
*Average pistil length.*—11/16" [17.5 mm.].
*Average stamen length.*—9/16" [14.3 mm.].
*Ovary.*—Smooth.
*Fragrance.*—Moderate.
*Pollen production.*—Moderate.
*Bloom density.*—Moderate.
*Number per cluster.*—2 to 6, average 3.
*Blooming period.*—Early to medium compared to other varieties, three days after 'Yummygem' plum (U.S. Plant Pat. No. 15,809).
*Onset of bloom.*—One percent on Feb. 11, 2016.
*Date of full bloom.*—Feb. 19, 2016.
*Duration of bloom.*—One to two weeks, dependent on ambient temperature.

FRUIT

Maturity when described: Firm ripe, Jun. 9, 2016.
Date of first picking: May 29, 2016.
Date of last picking: Jun. 12, 2016.
Size: Mostly uniform, large to medium.
*Average diameter axially.*—2 7/16" [61.9 mm.].
*Average diameter across cheek plane.*—2 13/16" [71.5 mm.].
*Average diameter across suture plane.*—2 11/16" [68.3 mm.].
*Typical weight.*—6.4 ounces [181 grams].
Form: Uniform, oblate, mostly symmetrical.
*Longitudinal section form.*—Oblate.
*Axial view form.*—Round.
Suture: A distinct Dark purplish red [259. d.pR] line located in a moderate trough extending from the base just to the apex with a slight depression beyond pistil point.
Ventral surface: Rounded, lightly lipped on both sides.
Lips: Fairly equal.
Cavity: Circular, suture showing on one side.
*Depth.*—3/16" [4.8 mm.].
*Breadth.*—7/8" [22.2 mm.].
Base: Truncate, slightly cordate if viewed parallel to the suture.
Apex: Rounded to somewhat truncate.
Pistil point: A inconspicuous Light brown [57. l.Br] dot.
Stem: Medium.
*Average length.*—7/16" [11.1 mm.].
*Average width.*—1/8" [3.2 mm.].
Skin:
*Thickness.*—Medium.
*Surface.*—Smooth.
*Tenacity.*—Tenacious to the flesh.
*Astringency.*—Moderate.
*Tendency to crack.*—None observed.
*Color.*—Very deep red [14. v.deep R] with some Brilliant yellow green [116. brill.YG] streaking and strong Vivid greenish yellow [97. v.gY] freckling more toward the apex.
Flesh:
*Color.*—Moderate red [15. m.R] becoming Deep red [13. deep R] close to the skin and toward the stone with Strong red [12. s.R] fibers throughout.
*Surface of pit cavity.*—Covered with Deep red [13. deep R] broken fibers when twisted from stone.
*Amygdalin.*—Moderate to scarce.
*Juice.*—Abundant, rich.
*Texture.*—Firm, crisp.
*Fibers.*—Abundant, fine, tender.
*Ripens.*—Fairly even.
*Flavor.*—A tasty blend of acid and sugar, typically 16-18 brix.
*Aroma.*—Wanting.
*Eating quality.*—Very good.

STONE

Type: Clingstone.
Form: Oval.
Hilum: Narrow.
Base: Rounded.
Apex: Obtuse with a typical angle of 125 degrees with a very short tip.
Tip: Sharp, about 1/16" [1.6 mm.] in length.
Sides: Unequal.
Surface: Irregularly furrowed near base.
External color of stone: Moderate orange [53. m.O].
Pit wall color when cracked: Pale yellow [89. p.Y].
Cavity surface color: Dark orange yellow [72. d.OY].
Average pit wall thickness: 1/8" [3.2 mm.].
Average length: 1" [25.4 mm.].
Average width: 7/8" [22.2 mm.].
Average breadth: 7/16" [11.1 mm.].
Tendency To split: None observed.
Kernel:
*Form.*—Oval.
*Skin color.*—Pale yellow [89. p.Y] when first removed.
*Pellicle color.*—Vivid yellow [82. v.Y].
*Vein color.*—Brilliant yellow [83. brill.Y].
*Taste.*—Bitter.
*Viable.*—Yes.
*Average length.*—9/16" [14.3 mm.].
*Average width.*—7/16" [11.1 mm.].
*Amygdalin.*—Moderate.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *Prunus salicina*, substantially as illustrated and described, that is most similar to 'Plumsweet VI' interspecific tree (U.S. Plant Pat. No. 18,687), by being self-unfruitful and by producing fruit that ripens in the early season and that is a red and green two-tone with freckles in skin color, clingstone in type, firm in texture, juicy, and sweet in flavor, but is distinguished therefrom by being easier to set and by producing fruit that is larger in size and darker red in flesh color.

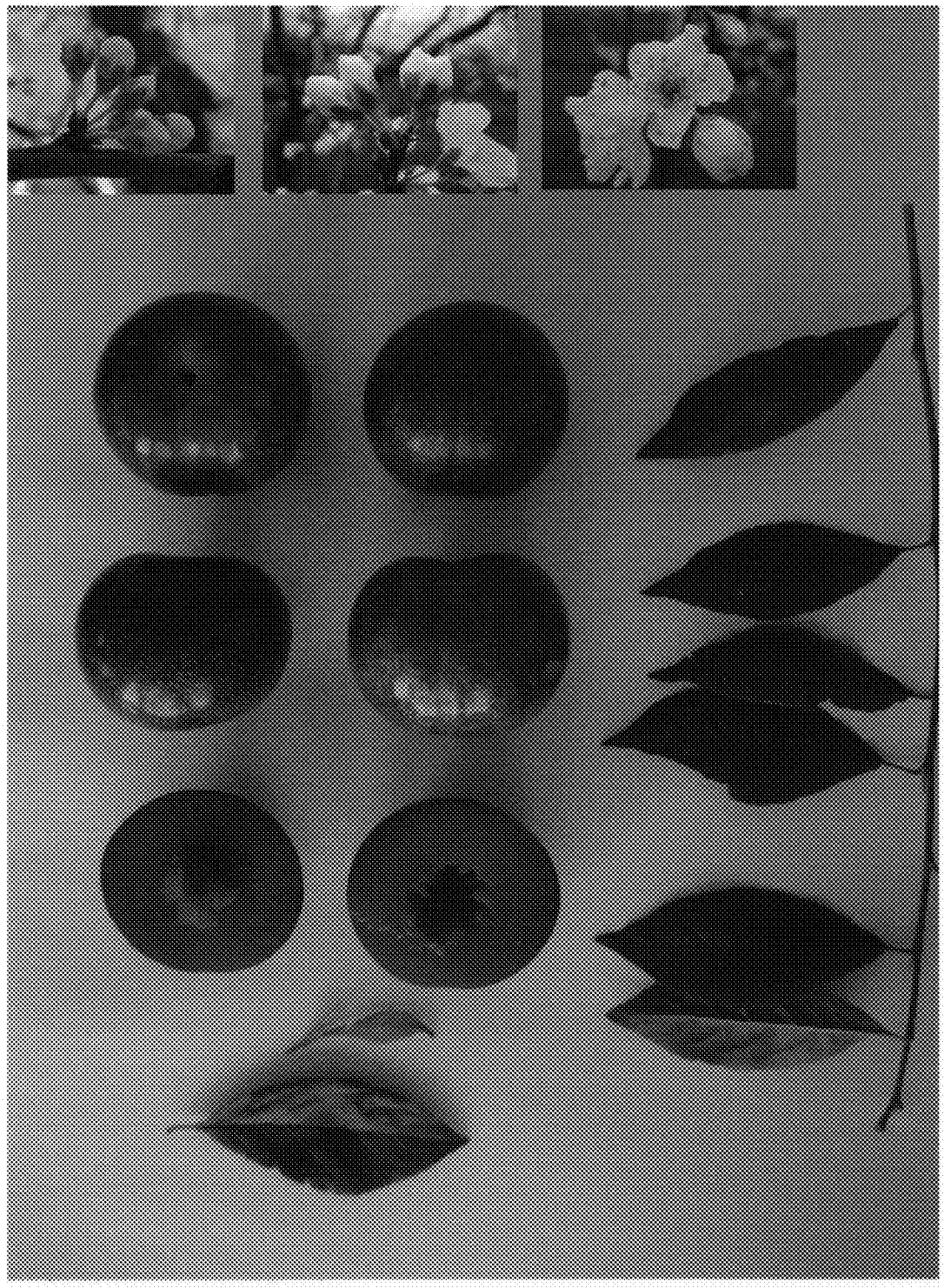

* * * * *